United States Patent
Wang et al.

(10) Patent No.: US 6,348,621 B1
(45) Date of Patent: *Feb. 19, 2002

(54) PROCESS FOR THE CARBONYLATION OF ETHYLENE AND CATALYST SYSTEM FOR USE THEREIN

(75) Inventors: Xiao Lan Wang, Acton; Robert Paul Tooze, Cleveland; Keith Whiston; Graham Ronald Eastham, both of Co Durham, all of (GB)

(73) Assignee: Imperial Chemical Industries PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/860,159

(22) PCT Filed: Dec. 22, 1995

(86) PCT No.: PCT/GB95/03021

§ 371 Date: Oct. 13, 1999

§ 102(e) Date: Oct. 13, 1999

(87) PCT Pub. No.: WO96/19434

PCT Pub. Date: Jun. 27, 1996

(30) Foreign Application Priority Data

Dec. 22, 1994 (GB) .............................................. 9425911

(51) Int. Cl.$^7$ ................................................ C07C 67/36
(52) U.S. Cl. ...................................................... 560/232
(58) Field of Search .......................................... 566/233

(56) References Cited

U.S. PATENT DOCUMENTS 4,269,781 A * 5/1981 Vanderspurt et al.
4,960,926 A * 10/1990 Drent
5,364,957 A * 11/1994 Arnoldy et al.

OTHER PUBLICATIONS

Keim et al. (J. Organomet. Chem.; 1996; 514(1–2), pp. 271–276).*

* cited by examiner

*Primary Examiner*—Gary Geist
*Assistant Examiner*—Robert W. Deemie
(74) *Attorney, Agent, or Firm*—Pillsbury Winthrop LLP

(57) ABSTRACT

A catalyst system capable of catalyzing the carbonylation of ethylene and a process which uses such a system wherein the catalyst system is obtainable by combining a metal of Group VIII, e.g., palladium, or a compound thereof and a bidentate phosphine, e.g. bis(di-t-butyl phospino)-o-xylene, according to the equation $C_2H_4+CO+ROH \rightarrow C_2H_5CO_2R$,.

9 Claims, No Drawings

PROCESS FOR THE CARBONYLATION OF ETHYLENE AND CATALYST SYSTEM FOR USE THEREIN

FIELD OF THE INVENTION

The invention relates to the carbonylation of ethylene using carbon monoxide in the presence of a catalyst system and to such a catalyst system.

BACKGROUND OF THE INVENTION

The carbonylation of ethylene using carbon monoxide in the presence of an alcohol or water and a catalyst system comprising a Group III metal, e.g. palladium and a phosphine ligand, e.g. an alkyl phosphine, cycloalkyl phosphine, aryl phosphine, pyridyl phosphine or bidentate phosphine, has been described in numerous European patents and patent applications, e.g. EP-A0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable higher reaction rates to be achieved.

The main problem with the previously disclosed catalyst systems is that, although relatively high reaction rates can be achieved, the palladium catalyst dies off quickly which necessitates the frequent replenishment of the catalyst and hence results in a process which is industrially unattractive.

DETAILED DESCRIPTION OF THE INVENTION

It has now been found that a particular group of bidentate phosphine compounds can provide remarkably stable catalysts which require little or no replenishment; that use of such bidentate catalysts leads to reaction rates which are significantly higher than those previously disclosed; that little or no impurities are produced at high conversions.

Accordingly, the present invention provides a process for the carbonylation of ethylene which process comprises reacting ethylene with carbon monoxide in the presence of a source of hydroxyl groups and of a catalyst system, wherein the catalyst system is obtainable by combining:

(a) a metal of Group VIII or a compound thereof; and
(b) a bidentate phosphine of general formula (I)

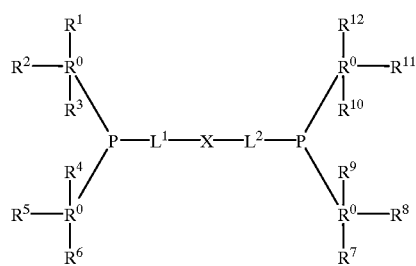

(I)

wherein
$R^0$ is a tertiary carbon atom
each of $R^1, R^2, R^3, R^4, R^5, R^6, R^7, R^8, R^9, R^{10}, R^{11}$ and $R^{12}$ is independently a pendant optionally substituted organic group which carries a carbon atom through which the group is linked to the respective $R^0$;
each of $L^1$ and $L^2$ is independently a linking group selected from an optionally substituted lower alkylene chain connecting the respective phosphorus atom to the group X; and
X is a bridging group comprising an optionally substituted aryl moiety to which the phosphorus atoms are linked on available adjacent carbon atoms.

In a second aspect, the present provides a catalyst system capable of catalysing the carbonylation of ethylene, which catalyst system is formed from
(a) a metal of Group VIII or a compound thereof; and
(b) a bidentate phosphine of general formula (I)

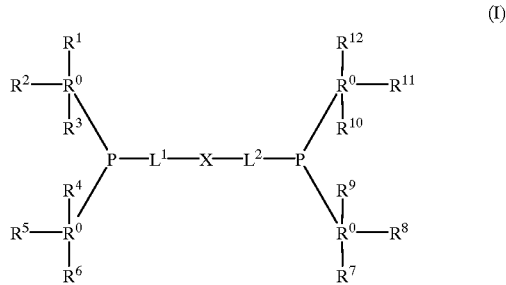

(I)

wherein
$R^0$ is a tertiary carbon atom
each of $R^1, R^2, R^3, R^4, R^5, R^6, R^7, R^8, R^9, R^{10}, R^{11}$ and $R^{12}$ is independently a pendant optionally substituted organic group which carries a carbon atom through which the group is linked to the respective $R^0$;
each of $L^1$ and $L^2$ is independently a linking group selected from an optionally substituted lower alkylene chain connecting the respective phosphorus atom to the group X; and
X is a bridging group comprising an optionally substituted aryl moiety to which the phosphorus atoms are linked on available adjacent carbon atoms.

The pendant optionally substituted organic groups, $R^1, R^2, R^3, R^4, R^5, R^6, R^7, R^8, R^9, R^{10}, R^{11}$ and $R^{12}$, may be independently selected from a wide range of components. Preferably, the pendant groups are optionally substituted lower alkyl, e.g. $C_{1-8}$, and which may be branched or linear. Particularly preferred is when the organic groups, $R^1, R^2, R^3, R^4, R^5, R^6, R^7, R^8, R^9, R^{10}, R^{11}$ and $R^{12}$, when associated with their respective $R^0$ carbon atom form composite groups which are at least as sterically hindering as t-butyl. Steric hindrance in this context is as discussed at page 14 et seq of "Homogeneous Transition Metal Catalysis—A Gentle Art", by C Masters, published by Chapman and Hall, 1981.

The linking groups, $L^1$ and $L^2$, are independently selected from an optionally substituted, particularly lower alkyl, e.g. $C_1$ to $C_4$, substituted, lower alkylene, e.g. $C_1$ to $C_4$ chain. Especially preferred is when both $L^1$ and $L^2$ are methylene.

The bridging group X is an aryl moiety, e.g. a phenyl group, which may be optionally substituted, provided that the two phosphorus atoms are linked to adjacent carbon atoms, e.g. at the 1 and 2 positions on the phenyt group. Optional substitution of the aryl moiety may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene.

Examples of suitable bidentate ligands are bis(di-t-butyl phosphino)-o-xylene (also known as 1,2 bis(di-t- butylphosphinomethyl)benzene), bis(di-t-neopentyl phosphino)-o-xylene and bis 1,2(di-t-butyl phosphino) naphthalene. Additionally, the bidentate phosphine may be bonded to a suitable polymeric substrate via at least one of the bridging group X, the linking group $L^1$ or the linking group $L^2$, e.g. bis(di-t-butyl phosphino)-o-xylene may be bonded via the xylene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group VIII metal present is from 1 to 50, e.g. 1 to 10 and particularly from 1 to 5 mol per mol.

The carbon monoxide may be used in the presence of other gases which are inert in the reaction. Examples of such gases include hydrogen, nitrogen, carbon dioxide and the noble gases such as argon.

The process of the present invention is preferably carried out at a temperature from 20 to 250° C., in particular from 40 to 150° C. and especially from 70 to 120° C.

The process may be conducted under a total pressure of from $1 \times 10^5$ to $100 \times 10^5$ $N.m^{-2}$ and in particular from $5 \times 10^5$ to $50 \times 10^5$ $N.m^{-2}$.

Suitable Group VIII metals include cobalt, nickel, palladium, rhodium and platinum. Particularly preferred is palladium. Suitable compounds of such Group VIII metals include salts of such metals with, or compounds comprising weakly coordinated anions derived from, nitric acid; sulphunc acid; lower alkanoic (up to $C_{12}$) acids such as acetic acid and propionic acid; sulphonic acids such as methane sulphonic acid, chlorosulphonic acid, fluorosulphonic acid, trifluoro methane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; perfluororated carboxylic acid such as trichloroacetic acid and trifluoroacetic acid; orthophosphoric acid; phosphonic acid such as benzene phosphonic acid; and acids derived from interactions between Lewis acids and Broensted acids. Other sources which may provide suitable anions include the tetraphenyl borate derivatives. Additionally, zero valent palladium compounds with labile ligands, e.g. tri(dibenzylideneacetone) dipalladium, may be used.

The catalyst system of the present invention may be used homogeneously or heretogeneously. Preferably the catalyst system is used homogeneously.

The catalyst system of the present invention is preferably constituted in the liquid phase which may be formed by one or more of the reactants or by the use of a suitable solvent.

Suitable solvents that may be used in conjunction with the catalyst system include one or more aprotic solvents such as ethers, e.g. diethyl ether, dimethyl ether, dimethyl ether of diethylene glycol, anisole and diphenyl ether; aromatic compounds, including halo variants of such compounds, e.g. benzene, toluene, ethyl benzene, o-xylene, m-xylene, p-xylene, chlorobenzene, o-dichlorobenzene, m-dichlorobenzene, and p-dichlorobenzene; alkanes, including halo variants of such compounds, e.g. hexane, heptane. 2,2,3-trimethylpentane, methylene chloride and carbon tetrachloride; nitrites, e.g. benzonitrile and acetonitrile; esters, e.g. methyl benzoate, methyl acetate and dimethyl phthalate; sulphones, e.g. diethyl sulphone and tetrahydrothiophene 1,1-dioxide; amides, including halo variants of such compounds, e.g. dimethyl formamide and N-methyl pyrrolidone.

The catalyst system of the present invention is particularly suited to the carbonylation of ethylene. Surprisingly, propane has been found to be difficult to carbonylate to the extent that the present catalyst system may be viewed as not being able to carbonylate propane.

The end product of the reaction is determined at least in part by the source of hydroxyl groups that is used. The use of water gives rise to the corresponding carboxylic acid whereas the use of an alkanol leads to the corresponding ester. Suitable alkanols include $C_{1-30}$ alkanols, optionally substituted with one or more substituents such as halogen atoms, cyano, carbonyl, alkoxy or aryl groups. Suitable alkanols include methanol, ethanol, propanol, 2-propanol, 2-butanol, t-butyl alcohol and chlorocapryl alcohol. Particularly useful are methanol and ethanol.

The molar ratio of the amount of ethylene used in the reaction to the amount of hydroxyl providing compound is not critical and may vary between wide limits, e.g. from 0.001:1 to 100:1 mol/mol.

The product of the reaction may be separated from the other components by any suitable means. However, it is an advantage of the present catalyst system that significantly fewer by-products are formed thereby reducing the need for further purification after the initial separation of the product as may be evidenced by the generally significantly higher selectivity. A further advantage is that the other components which contain the catalyst system which may be recycled and/or roused in further reactions with minimal supplementation of fresh catalyst.

EXAMPLES

The following Examples further illustrated the present invention.

Example 1

In this example methyl propionate was prepared from carbon monoxide and ethylene using methanol as the hydroxyl group source.

A mechanically stirred autoclave of 2 litre capacity was evacuated of air and town charged with a catalyst system consisting of

| | |
|---|---|
| methanol | 300 cm$^3$ |
| palladium acetate | 0.1 mmol |
| bidentate* | 0.3 mmol |
| methane sulphonic acid | 0.24 mmol |

*bis (di-t-butylphosphino)-o-xylene

Carbon monoxide and ethylene on an equimolar basis was introduced until a pressure of $30 \times 10^5$ $N.m^{-2}$ was reached. The temperature of the reactor was raised to and maintained at 100° C. As the reaction proceeded sufficient additional methanol was introduced to compensate for that which had been consumed and additional carbon monoxide and ethylene was added (on an equimolar basis) to maintain the pressure. No palladium precipitation was observed.

Example 2

Comparative

Example 1 was repeated except that the propane analogue of the o-xylene bidentate was used. Precipitation of palladium, with consequent deactivation of the catalyst, was observed within two hours.

The reaction rate (expressed as mole ethylene per mole of palladium per hour), selectivity to methyl propionate (% by gas chromatography) and turn over number based on phosphine (expressed as mole methyl propionate per mole of phosphine) for each of the catalyst systems described in Examples 1 and 2 is shown in Table 1 below.

TABLE 1

| PHOSPHINE LIGAND | REACTION RATE | SELECTIVITY | TURN OVER NUMBER |
|---|---|---|---|
| bis (di-t-butyl phosphino)-o-xylene | 40000 | 99.95 | >50000 |
| bis (di-t-butyl phosphino)-propane | 15000 | 98.00 | 1700 |

It can thus be seen that the catalyst system of the present invention is more stable, more reactive and more selective than the conventional bidentate system.

Example 3

The catalyst system from Example 1 was extracted at the end of the procedure and reused with fresh methanol and methane sulphonic acid. The activity of the reused catalyst was the same as that of the original. The catalyst system of Example 2 was unable to be reused due to the precipitation of the palladium.

Example 4

Example 1 was repeated using the 4-nitro substituted analogue of the bidentate ligand which was prepared via the phosphonium salt produced from the reaction of the appropriate secondary phosphine with the corresponding aromatic dihalide.

Example 5

Example 4 was repeated using the 4-methoxy substituted analogue. The results of Examples 4 and 5 were as follows:

| PHOSPHINE LIGAND | REACTION RATE | SELECTIVITY | TURN OVER NUMBER |
|---|---|---|---|
| 4-nitro | 36000 | 99.9 | >25000 |
| 4-methoxy | 37000 | 99.9 | >25000 |

Example 6

Example 1 was repeated except that an alternative source of palladium was used. The catalyst was prepared by mixing the bidentate phosphine, tris(dibenzylideneacetone) dipalladium known as dba, and sulphonic acid in a molar ratio of 2:1:3. The phosphine and dba were mixed together prior to the addition of the acid.

The reaction was conducted using an equimolar mixture of methanol and methyl propionate at a total pressure of 15 barg (using a 1:1 mixture of carbon monoxide and ethylene). The reaction temperature was 80° C.

Example 7

Example 6 was repeated except that in the ligand one of the t-butyl groups on each phosphorous atom was replaced by cyclohexyl groups.

Example 8

Example 6 was repeated except that in the ligand the t-butyl groups were replaced by cyclohexyl groups.

Example 9

Example 6 was repeated except that in the ligand the t-butyl groups were replaced by isopropyl groups.

Example 10

Example 6 was repeated except that in the ligand the t-butyl groups were replaced by phenyl groups.

Example 11

Example 6 was repeated except that the linking methylene groups were both replaced by oxygen atoms. The phosphinite was synthesised from an aromatic diol and chloro di(t-butyl) phosphine.

Example 12

Example 11 was repeated except that the 4 t-butyl substituted analogue of the ligand was used.

The results of Examples 6 to 12 were as follows:

| PHOSPHINE LIGAND | REACTION RATE | SELECTIVITY | TURN OVER NUMBER |
|---|---|---|---|
| Example 6 | 12000 | 99.95 | >250000 |
| Example 7 | 500 | 30 | >1500 |
| Example 8 | 200 | 25 | >600 |
| Example 9 | 200 | 20 | 500 |
| Example 10 | 400 | 20 | >1200 |
| Example 11 | 100 | 30 | <300 |
| Example 12 | 100 | 30 | <300 |

What is claimed is:

1. A process for the carbonylation of ethylene which process comprises reacting ethylene with carbon monoxide in the presence of water or organic hydroxyl groups and of a catalyst system, wherein the catalyst system is obtainable by combining:

(a) a metal of Group VIII or a compound thereof; and (b) a bidentate phosphine of general formula (1)

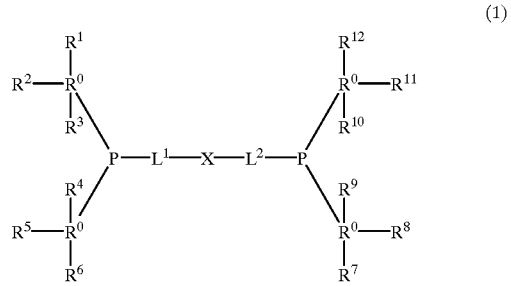

(1)

wherein $R^0$ is a tertiary carbon atom, each of $R^1$, $R^2$, $R^3$, $R^4$, $R^5$, $R^6$, $R^7$, $R^8$, $R^9$, $R^{10}$, $R^{11}$ and $R^{12}$ is independently a pendant optionally substituted organic group which carries a carbon atom through which the group is linked to the respective $R^0$;

each of $L^1$ and $L^2$ is independently a linking group selected from an optionally substituted alkylene chain connecting the respective phosphorus atom to the group X; and X is a bridging group comprising an optionally substituted aryl moiety to which the phosphorus atoms are linked on available adjacent carbon atoms.

2. A catalyst system capable of catalyzing the carbonylation of an ethylene, comprising:
(a) a metal of Group VIII or a compound thereof; and
(b) a bidentate phosphine of general formula (1)

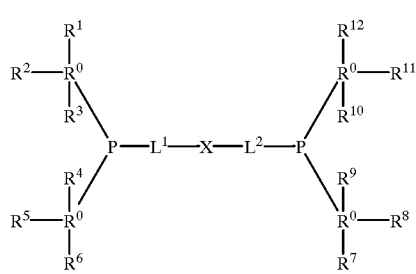

(1)

wherein
$R^0$ is a tertiary carbon atom,
each of $R^1, R^2, R^3, R^4, R^5, R^6, R^7, R^8, R^9, R^{10}, R^{11}$ and $R^{12}$ is independently a pendant optionally substituted organic group which carries a carbon atom through which the group is linked to the respective $R^0$;
each of $L^1$ and $L^2$ is independently a linking group selected from an optionally substituted alkylene chain connecting the respective phosphorus atom to the group X; and
X is a bridging group comprising an optionally substituted aryl moiety to which the phosphorus atoms are linked on available adjacent carbon atoms.

3. A process as claimed in claim 1 wherein the pendant optionally substituted organic groups, $R^1, R^2, R^3, R^4, R^5, R^6, R^7, R^8, R^9, R^{10}, R^{11}$ and $R^{12}$, are independently selected from optionally substituted lower alkyl.

4. A process as claimed in claim 1 wherein the organic groups, $R^1, R^2, R^3, R^4, R^5, R^6, R^7, R^8, R^9, R^{10}, R^{11}$ and $R^{12}$, are associated with their respective $R^0$ carbon atom so as to form composite groups which are at least as sterically hindering as t-butyl.

5. A process as claimed wherein both $L^1$ and $L^2$ are methylene.

6. A catalyst system as claimed in claim 2 wherein the pendant optionally substituted organic groups, $R^1, R^2, R^3, R^4, R^5, R^6, R^7, R^8, R^9, R^{10}, R^{11}$ and $R^{12}$ are independently selected from branched or linear, optionally substituted $C_1$ to $C_8$ alkyl groups; and
wherein X is an aryl moiety optionally substituted, independently, by: a $C_1$ to $C_8$ alkyl, aryl alkoxy, carbaloxy, halo, nitro, trihalomethyl or cyano group; and
$L^1$ and $L^2$ are independently, an optionally substituted $C_1$ to $C_4$ alkyl group.

7. A catalyst system as claimed in claim 2 wherein the organic groups, $R^1, R^2, R^3, R^4, R^5, R^6, R^7, R^8, R^9, R^{10}, R^{11}$ and $R^{12}$ are associated with their respective $R^0$ carbon atom so as to form composite groups which are at least as sterically hindering as t-butyl; and
wherein X is an aryl moiety optionally substituted, independently, by: a $C_1$ to $C_8$ alkyl, aryl alkoxy, carbaloxy, halo, nitro, trihalomethyl or cyano group; and
$L^1$ and $L^2$ are independently, an optionally substituted $C_1$ to $C_4$ alkyl group.

8. A catalyst system as claimed in claim 2 wherein $R^1, R^2, R^3, R^4, R^5, R^6, R^7, R^8, R^9, R^{10}, R^{11}$ and $R^{12}$ is independently a pendant optionally substituted lower alkyl group when carries a carbon atom through which the group is linked to the respective $R^0$.

9. A catalyst system as claimed in claim 2 wherein at least one of the organic groups $R^1, R^2, R^3, R^4, R^5, R^6, R^7, R^8, R^9, R^{10}, R^{11}$ and $R^{12}$ sterically hinder the resepective $R^0$ at least as must as a t-butyl group.

* * * * *